United States Patent

Sakakibara et al.

[11] Patent Number: 4,803,301
[45] Date of Patent: Feb. 7, 1989

[54] PROCESS FOR PRODUCING OPTICALLY ACTIVE 2-PHENOXYPROPIONIC ACID

[75] Inventors: Masayuki Sakakibara; Yasushi Nii, both of Maebashi, Japan

[73] Assignee: Kirin Beer Kabushiki Kaisha, Tokyo, Japan

[21] Appl. No.: 181,078

[22] Filed: Apr. 13, 1988

[51] Int. Cl.$^4$ ............................................. C07C 59/12
[52] U.S. Cl. ................................................ 562/471
[58] Field of Search ................................... 562/471

[56] References Cited

U.S. PATENT DOCUMENTS

| | | | |
|---|---|---|---|
| 2,509,772 | 5/1950 | Leaper | 562/471 |
| 2,805,251 | 9/1957 | Marshall | 562/471 |
| 4,153,803 | 5/1979 | Thiele | 562/471 |
| 4,173,709 | 11/1979 | Metivier | 562/471 |
| 4,532,346 | 7/1981 | Rehn | 562/471 |
| 4,760,172 | 7/1988 | Tai | 562/471 |

FOREIGN PATENT DOCUMENTS 2123147  6/1987  Japan .

Primary Examiner—Paul J. Killos
Attorney, Agent, or Firm—Ladas & Parry

[57] ABSTRACT

There is provided a process for producing an optically active 2-phenoxypropionic acid, which comprises allowing an optically active lactic ester represented by the following formula (I) to react with a phenol represented by the following formula (II) in the copresence of a reagent A and a reagent B defined below to form an optically active 2-phenoxypropionic ester represented by the following formula (III), and liberating an optically active 2-phenoxypropionic acid represented by the following formula (IV) from the optically active 2-phenoxypropionic ester:

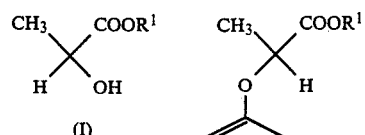

(I)

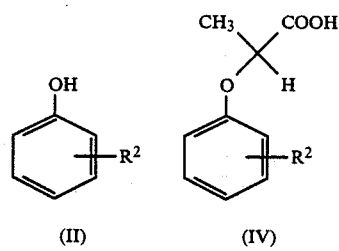

(III)

(II)

(IV)

wherein $R^1$ represents a group to form a monovalent ester, which can be eliminated from the compound (III) under weakly basic to acidic conditions and $R^2$ represents a hydrogen atom or 1 to 5 substituents which do not interfere in the reaction between the compounds (I) and (II); a reagent A being at least one compound selected from the group consisting of trialkylphosphine, trialkylphosphite, triarylphosphine and triarylphosphite; and a reagent B being at least one compound selected from the group consisting of dialkylazodicarboxylate and diarylazodicarboxylate.

6 Claims, No Drawings

PROCESS FOR PRODUCING OPTICALLY ACTIVE 2-PHENOXYPROPIONIC ACID

BACKGROUND OF THE INVENTION

1. Field of the Art

This invention relates to a process for producing an optically active 2-phenoxypropionic acid such as (2S)-(−)-2-(4'-chlorophenoxy)propionic acid, (2R)-(+)-2-(4'-chlorophenoxy)propionic acid, etc., more particularly to a process for producing an optically active 2-phenoxypropionic acid steroselectively from an optically active lactic ester.

2. Prior Art

A 2-phenoxypropionic acid such as (2S)-(−)-2-(4'-chlorophenoxy)propionic acid and (2R)-(+)-2-(4'-chlorophenoxy)propionic acid is a useful substance having the action of reducing serum lipid, and a process for production thereof has been already reported (D. T. WITIAK et al., J. Med. Chem., 11 (5) 1086 (1968)). However, this process comprises synthesizing a racemic form of 2-(4'-chlorophenoxy)propionic acid and subjecting this to optical resolution, and therefore it has been difficult to produce 2-(4'-chlorophenoxy)propionic acid efficiently in a high optical purity.

SUMMARY OF THE INVENTION

The present invention provides a process for producing an optically active 2-phenoxypropionic acid efficiently in a steroselective manner of chemical synthesis.

More specifically, the process for producing an optically active 2-phenoxypropionic acid according to the present invention comprises: allowing an optically active lactic ester represented by the following formula (I) to react with a phenol represented by the following formula (II) in the co-presence of a reagent A and a reagent B defined below to form an optically active 2-phenoxypropionic ester represented by the following formula (III), and liberating an optically active 2-phenoxypropionic acid represented by the following formula (IV) from the optically active 2-phenoxypropionic ester:

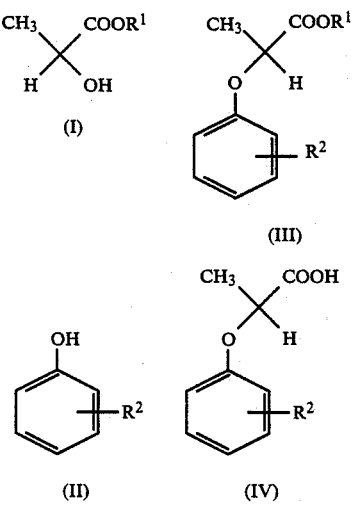

wherein $R^1$ represents a group to form a monovalent ester, which can be eliminated from the compound (III) under weakly basic to acidic conditions and $R^2$ represents a hydrogen atom or 1 to 5 substituents which do not interfere in the reaction between the compounds (I) and (II); a reagent A being at least one compound selected from the group consisting of trialkylphosphine, trialkylphosphite, triarylphosphine and triarylphosphite; a reagent B being at least one compound selected from the group consisting of dialkylazodicarboxylate and diarylazodicarboxylate.

According to the present invention, an optical active 2-phenoxypropionic acid can be produced stereospecifically from an inexpensive optically active lactic ester as a starting material through a simple sequence of operations in a higher yield than a 40% yield.

In the aforementioned known process, according to the same literature, (2S)-(−)-2-(4'-chlorophenoxy)propionic acid was prepared through optical resolution with brucine from a racemic form which was obtained by condensation of sodium salt of p-chlorophenol with ethyl 2-bromopropionate, and in this case, the yield of the optically active compound was at most about 10%.

As to other points, see the paragraph, "Characteristics of the Reaction according to the Present Invention", as described below.

DETAILED DESCRIPTION OF THE INVENTION

The optically active 2-phenoxypropionic acid, the target compound in the present invention, is produced from an optically active lactic ester through the reaction with a phenol under prescribed conditions, followed by the treatment of an optically active 2-phenoxypropionic ester thus obtained with an acid to liberate it.

Characteristics of the Reaction according to the Present Invention

The present invention has succeeded in obtaining an optically active 2-phenoxypropionic acid compound all at once without a process of optical resolution of a racemic form, on the basis of the finding of the reaction route to keep the optical purity of the starting lactic ester with the prescribed reagents of A and B, using a phenol as a source of the phenoxy moiety and a lactic ester as a source of the propionic moiety to construct the 2-phenoxypropionic skeleton.

It was similar in the aforementioned known process that the 2-phenoxypropionic skelton was constructed through the coupling of a phenolic compound with a $C_3$-carboxylic compound. However, according to the known process where NaBr was eliminated from a phenol salt used as a phenolic compound and 2-bromopropionic ester used as a $C_3$-carboxylic compound, the 2-phenoxypropionic skeleton was constructed though the product was obtained as a racemic form. In contrast, in the present invention, a phenolic compound having a free phenolic hydroxyl group and a lactic ester as a $C_3$-carboxylic compound are used and a stereo-controlled reaction accompanied with bond formation of an asymmetric carbon can be carried out by the application of dehydration reaction with the prescribed reagents A and B.

From such characteristics of the present reaction and the fact that the essence of the present invention resides in the purposeful application of this reaction, the characteristics of the substituents $R^1$ and $R^2$ in the two starting compounds can be said to be naturally defined. More specifically, since the reaction cannot proceed well if the lactic compound which is one of the starting substances is an acid, the lactic compound must be an ester, and since the 2-phenoxypropionic compound which is the target compound should necessarily be a free propionic acid, the group $R^1$ to form an ester must be eliminated from the ester intermediate once formed. Elimination of the group to form an ester can be performed by, for example, hydrolysis. When hydrolysis is performed under strongly alkaline conditions, there is the possibility that the optical activity is spoilt. Accordingly, the group $R^1$ to form an ester in the starting lactic ester may be any group to form a monovalent ester, provided the group $R^1$ prescribes the starting lactic compound for an ester as a proto-type of an acid, does not interfere in the reaction with the phenolic compound and can be eliminated under the conditions other than strongly alkaline condition, namely weakly basic to acidic conditions.

The phenolic compounds which is another starting substance may possess any substituent which does not interfere in the reaction with the lactic ester. The group $R^2$ may be said to be different in character from $R^1$ in that while $R^1$ is merely a protective group for the carboxylic group of lactic acid, $R^2$ is such one that its presence is intentionally desired in the compound (IV).

Optically active lactic ester

The optically active lactic ester to be used in the present invention is represented by the following formula (I), and it can be a (D)-(−)-lactic ester or an (L)-(+)-lactic ester.

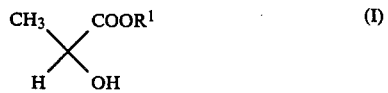 (I)

The group $R^1$ is as defined above. Some specific examples are: an alkyl having 1 to 8 carbon atoms, benzyl, p-bromobenzyl, o-nitrobenzyl, p-nitrobenzyl, p-methoxybenzyl, methoxymethyl, methylthiomethyl, tetrahydropyranyl, tetrahydrofuranyl, methoxyethoxymethyl, benzyloxymethyl, phenacyl, p-bromophenacyl, α-methylphenacyl, p-methoxyphenacyl, diacylmethyl ("acyl" is inclusive of alkoxycarbonyl other than alkylcarbonyl, including specifically lower alkyl, phenyl, lower-alkylphenyl, and lower alkoxy), N-phthalimidomethyl, 2,2,2-trichloroethyl, 2-haloethyl, ω-chloroalkyl (about $C_2$–$C_8$, particularly $C_4$ or $C_5$), 2-(trimethylsilyl)ethyl, 2-methylthioethyl, 2-(p-nitrophenylsulphenyl)ethyl, 2-(p-toluenesulfonyl)ethyl, t-butyl, allyl, cinnamyl, phenyl and lower-alkylphenyl, p-methylthiophenyl, triphenylmethyl, diphenylmethyl, bis(o-nitrophenyl)methyl, 9-anthrylmethyl, 2,4,6-trimethylbenzyl, triethylsilyl, t-butyldimethylsilyl, i-propyldimethylsilyl and phenyldimethylsilyl.

Phenol

The phenol to be used in the present invention is represented by the following formula (II):

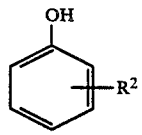 (II)

$R^2$ is as defined above. Since phenol has 5 substitutable sites, $R^2$ can exist in a number of 1 to 5 on the phenolic compound, as a matter of course. Some specific examples of $R^2$ are: a halogen (particularly chlorine), hydrogen, nitro, alkoxy, aryloxy, thioalkoxy, cyano, aryl, acyl, alkylsulfonyl, alkoxycarbonyl, acylamino, alkyl and sulfonylamino. Here, the term, "alkyl" or "alkoxy", means alkyl or alkoxy having about 1 to 10 carbon atoms, and the term, "aryl", means phenyl or substituted phenyl. The term, "acyl", represents the same meaning as above mentioned for an alkyl group when it is aliphatic and for an aryl group when it is aromatic.

Reagent A and Reagent B

The reagent A is trialkylphosphine, trialkylphosphite, triarylphosphine, or triarylphosphite. Here, "alkyl" and "aryl" have the same meanings as defined for the compounds (I) and (II).

Specific examples are one kind or more kinds selected from the group consisting of trialkylphosphines such as tributylphosphine and trioctylphosphine, triarylphosphines such as triphenylphosphine, trialylphosphites such as triethylphosphite and trimethylphosphite, triarylphosphites such as triphenylphosphite.

The terms, "alkyl" and "aryl" of dialkylazodicarboxylate and diarylazodicarboxylate as the reagent B have also the same meanings as above, and specific examples are diethylazodicarboxylate, dimethylazodicarboxylate, and diphenylazodicarboxylate.

Reaction Conditions

In the present invention, an optically active lactic ester is allowed to react with a kind of phenol in the co-presence of the reagents A and B to form an optically active 2-phenoxypropionic ester under the conditions described below.

This reaction can be carried out generally in an inert solvent. Solvents which can be used are preferably those capable of dissolving partially at least one of the reaction components, specific examples being tetrahydrofuran, diethyl ether, methylene chloride and benzene.

The concentration of the optically active lactic ester and the amounts of the phenol, reagents A, and B at the initiation of the reaction are both not critical. However, the concentration of the optically active lactic ester is generally 0.1 to 2 moles and the amounts of the phenol, the reagents A, and B are preferably 1 to 5 moles for the phenol, 1 to 5 moles for the reagent A, and 1 to 5 moles for the reagent B based on 1 mole of the optically active lactic ester.

The reaction temperature is also not critical, and the reaction can be carried out generally within the range of the temperature from the freezing point to the boiling point of the solvent used. In the present reaction, since concurrent inversion with phenoxidation of the optically active lactic ester occurs on the asymmetric carbon, (2S)-2-phenoxypropionic ester is obtained from (D)-(−)-lactic ester and (2R)-phenoxypropionic ester from (L)-(+)-lactic ester (see the schemes shown below). This reaction can be completed generally in 0.5 to 48 hours under the above mentioned conditions.

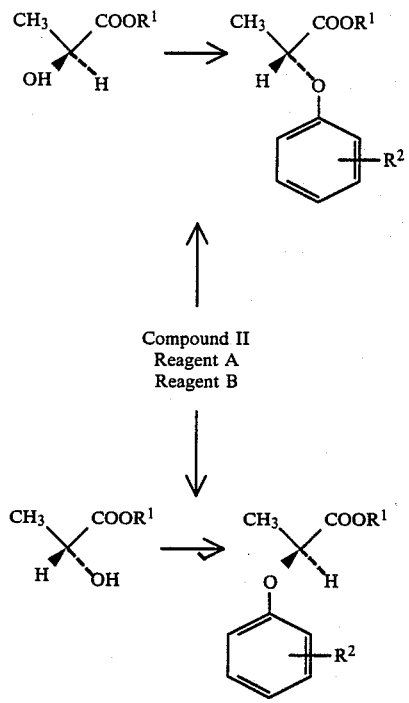

Compound II
Reagent A
Reagent B

The optically active 2-phenoxypropionic ester thus formed is purified according to a conventional method, if necessary, and then the purified product is subjected to hydrolysis, reductive ester cleavage or hydrogenolysis to liberate the acid, whereby an optically active 2-phenoxypropionic acid can be obtained.

Purification from reaction products of the optically active 2-phenoxypropionic ester and the optically active 2-phenoxypropionic acid which is the target substance of the present invention can be practiced by any purposeful means as conventionally used in the field of organic synthetic chemistry. Specifically, it can be easily performed by silica gel chromatography, recrystallization, distillation, etc.

For the reaction to liberate the optically active 2-phenoxypropionic acid from the optically active 2-phenoxypropionic ester, any ester cleavage reaction conventionally used in the field of organic synthetic chemistry can be employed. Specifically, it can be practiced easily by hydrolysis with an acid such as trifluoroacetic acid, p-toluenesulfonic acid, sulfuric acid and perchloric acid by reductive ester cleavage with zinc-acetic acid, or by hydrogenolysis using a catalyst.

EXPERIMENTAL EXAMPLES

Example 1

To a stirred solution of known tert-butyl D-(−)-lactate (160 mg), 4-chlorophenol (108 μl) and triphenylphosphine (287 mg) in dry tetrahydrofuran (6 ml) on an ice bath, diethylazodicarboxylate (173 μl) was added dropwise over about 5 minutes. After the addition, the ice bath was removed and the mixture was further stirred at room temperature for 3 hours. The reaction mixture was then evaporated with a rotary evaporator (water bath temperature 25° C.). The residue thus obtained was purified by silica gel chromatography [silica gel 30 g, eluant:ethyl acetate-hexane (1:10)] to give tert-butyl (2S)-(−)-2-(4′-chlorophenoxy)-propionate (173 mg).

IR$v_{max}^{film}$ (cm$^{-1}$): 3050, 2975, 2950, 1730, 1595, 1495, 1370, 1240, 1160, 1150, 1090, 825

FD-MS: 256, 258 (M+, peak intensity 3:1)

Elemental analysis: ($C_{13}H_{17}ClO_3$) Calcd. (%): C: 60.82, H: 6.67, Cl: 13.81, O: 18.70; Found (%): C: 60.80, H: 6.69, Cl: 13.86, O: 18.65.

To a stirred solution of tert-butyl (2S)-(−)-2-(4′-chlorophenoxy)-propionate obtained (173 mg) in methylene chloride (3 ml) on an ice bath, trifluoroacetic acid (0.5 ml) was added. After 15 minutes, the ice bath was removed and the mixture was stirred at room temperature for an additional hour. The reaction mixture was evaporated under reduced pressure. The residue thus obtained was purified by silica gel chromatography [silica gel 7.8 g, eluant:ethyl acetate-hexane (1:10) and then ethyl acetate] to give colorless crystals of (2S)-(−)-2-(4′-chlorophenoxy)propionic acid (91 mg).

m.p. 102°–102.5° C. (recrystallized from etherhexane).

$[\alpha]_D^{27}$ −35.6° (C 0.95, MeOH).

Literature value, $[=_D^{25}$ −34.96° (C 5.0078, MeOH), J. Med. Chem., 11, 1086(1968)].

IR$v_{max}^{KBr}$ (cm$^{-1}$): 3400, 2950, 1720, 1595, 1495, 1280, 1230, 1170, 1130, 1095, 1045, 825.

$^1$H-NMR(CDCl$_3$, 100 MHz) δ: 1.66 (d, J=7 Hz, 3H), 4.76 (q, J=7 Hz, 1H), 6.83 (d, J=9 Hz, 2H), ca. 7.0 (br, 1H), 7.26 (d, J=9 Hz, 2H).

FD-MS: 200, 202 (M+, peak intensity 3:1).

Elemental analysis: ($C_9H_7ClO_3$) Calcd. (%): C: 53.88, H: 4.52, Cl: 17.67, O: 23.73; Found (%): C: 53.85, H: 4.56, Cl: 17.70, O: 23.87.

EXAMPLE 2

To a stirred solution of known tert-butyl D-(−)-lactate (292 mg), 4-chlorophenol (197 μl) and triphenylphosphite (343 μl) in dry tetrahydrofuran (16 ml) on an ice bath, diethylazodicarboxylate (315 μl) was added dropwise over about 5 minutes. After the addition, the ice bath was removed and the mixture was further stirred at room temperature for 3 hours. The reaction mixture was evaporated with a rotary evaporator (water bath temperature 25° C.). The residue thus obtained was dissolved in ether (20 ml) and the ethereal solution was washed with water. Ether was evaporated. The residue obtained was then purified by silica gel chromatography [silica gel 55 g, eluant:ethyl acetate-hexane (1:10)] to give tert-butyl (2S)-(−)-2-(4′-chlorophenoxy)propionate (330 mg).

IR$v_{max}^{film}$ (cm$^{-1}$): 3050, 2975, 2950, 1730, 1595, 1494, 1370, 1240, 1160, 1150, 1090, 825.

To a solution of tert-butyl (2S)-(−)-2-(4′-chlorophenoxy)-propionate obtained (330 mg) in toluene (10 ml), p-toluenesulfonic acid hydrate (50 mg) was added. The mixture was heated at reflux temperaure for 1 hour. The reaction mixture was washed with water, dried over anhydrous sodium sulfate, and toluene was evaporated off under reduced pressure. The residue was purified by silica gel chromatography [silica gel 1.42 g, eluant:ethyl acetate-hexane (1:10) and then ethyl acetate] to give colorless crystals of (2S)-(−)-2-(4′-chlorophenoxy)propionic acid (183 mg). Physical data were identical with ones in Example 1.

Example 3

To a stirred solution of known tert-butyl L-(+)-lactate (217 mg), 4-chlorophenol (219 μl) and triphenylphosphine (584 mg) in dry tetrahydrofuran (8 ml) on an ice bath, diethylazodicarboxylate (350 μl) was added dropwise over about 10 minutes. After the addition, the ice bath was removed and the mixture was further stirred at room temperatures for 24 hours. The reaction mixture was evaporated with a rotary evaporator (water bath temperaure 38° C.). The residue thus obtained was purified by silica gel chromatography [silica gel 50 g, eluant:ethyl acetate-hexane (1:10)] to give tert-butyl (2R)-(+)-2-(4'-chlorophenoxy)propionate (256 mg).

FD-MS: 256, 258 (M+, Peak intensity 3:1).

Elemental analysis: ($C_{13}H_{17}ClO_3$) Calcd.: C: 60.82, H: 6.67, Cl: 13.81, O: 18.70; Found: C: 60.79, H: 6.69, Cl: 13.85, O: 18.67.

To a stirred solution of tert-butyl (2R)-(+)-2-(4'-chlorophenoxy)-propionate obtained (256 mg) in methylene chloride (5 ml), trifluoroacetic acid (1 ml) was added. After 15 minutes, an ice bath was removed and the mixture was stirred at room temperature for an additional hour. The reaction mixture was evaporated under reduced pressure. The residue thus obtained was purified by silica gel chromatography [silica gel 7.8 g, eluant:ethyl acetate-hexane (1:10) and then ethyl acetate] to give colorless crystals of (2R)-(+)-2-(4'-chlorophenoxy)propionic acid (148 mg).

m.p. 102.5°-103.0° C. (recrystallized from etherhexane).

$[\alpha]_D^{27}$ +35.9° (C 1.0, MeOH).

Literature value: $[\alpha_D^{25}+34.1°$ (C 3.6720, MeOH) J. Med. Chem., 11, 1986 (1968)]

FD-MS: 200, 202 (M+, Peak intensity 3:1).

Elemental anaysis ($C_9H_9ClO_3$): Calcd.: C: 53.88, H: 4.52, Cl: 17.67, O: 23.93; Found: C: 53.84, H: 4.57, Cl: 17.61, O: 23.98.

IR and NMR spectra were identical with ones in Example 1.

Example 4

To a stirred solution of known tert-butyl L-(+)-lactate (1.00 g), 4-(2',4'-dinitrophenoxy)phenol (2.08 g) and triphenylphosphine (1.98 g) in dry tetrahydrofuran (58 ml) on an ice bath, diethylazodicarboxylate (1.18 ml) was added dropwise. After the addition, the ice bath was removed and the mixture was further stirred at room temperature for 19 hours. The reaction mixture was evaporated with a rotary evaporator. The residue thus obtained was purified by silica gel chromatography [silica gel 344 g, eluant:ethyl acetate-hexane (1:5)] to give tert-butyl (2R)-(+)-2-(4'-(2",4"-dinitrophenoxy)-phenoxy]propionate (1.45 g). Since the product was decomosed even by high vacuum distillation, the viscous oily substance of the product thus obtained was left to stand at room temperature under high vacuum (0.25 Torr) for 2 hours, and then its physical data thereon were measured.

$[\alpha]_D^{28}$+34.7° (C 1.0, MeOH).

IR$\nu_{max}^{film}$(cm$^{-1}$): 3100 (w), 2990 (m), 2950 (w), 1740 (s), 1610 (s), 1545 (m), 1530 (s), 1503 (s), 1480 (s), 1460 (m), 1420 (w), 1395 (w), 1370 (m), 1345 (s), 1315 (w), 1275 (s), 1240 (s), 1190 (s), 1160 (s), 1135 (s), 1100 (m), 1070 (m), 1050 (m), 1010 (w), 950 (w), 930 (m), 920 (sh), 870 (w), 845 (s), 840 (s), 810 (w), 770 (w), 743 (m), 720 (w).

$^1$H-NMR (CDCl$_3$, 100 MHz)δ: 1.46 (s, 9H), 1.61 (d, J=7 Hz, 3H), 4.63 (q, J=7 Hz, 1H), 6.99 (d, J=7 Hz, 2H), 7.02 (d, J=7 Hz, 2H), 7.05 (d, J=9 Hz, 1H), 8.28 (dd, J=3 & 9 Hz, 1H), 8.80 (d, J=3 Hz, 1H),

FDMS(m/Z): 404 (M+).

Elemental analysis ($C_{19}H_{20}N_2O_8$): no satisfactory elemental analysis value could be obtained.

To a stirred solution of tert-butyl (2R)-(+)-2-[4'-(2",4"-dinitro-phenoxy)phenoxy]propionate thus obtained (1.00 g) in methylene chloride (12 ml) on an ice bath, trifluoroacetic acid (2 ml) was added. After 30 minutes, the ice bath was removed and the mixture was stirred at room temperature for additional 5.5 hours. The reaction mixture was evaporated under reduced pressure to give pale yellow crystals of (2R)-(+)-2-[4'-(2",4"-dinitrophenoxy)-phenoxy]propionic acid (0.76 g). A part of the crystals was recrystallized from hot ethyl acetate to give pale yellow crystals.

m.p.: 167°-169° C.

$[\alpha]_D^{29}$+29.1° (C 1.0, MeOH).

IR$\nu_{max}^{nujol}$ (cm$^{-1}$): 3300-2200 (br), 3080 (m), 2900 (s), 2850 (m), 1710 (s), 1670 (m), 1755 (sh), 1600 (s), 1520 (sh), 1515 (s), 1502 (s), 1478 (w), 1455 (s), 1365 (s), 1350 (s), 1275 (s), 1235 (s), 1220 (sh), 1195 (s), 1145 (m), 1135 (m), 1100 (w), 1070 (w), 1042 (m), 1008 (w), 920-895 (br), 870 (w), 835 (s), 800 (w), 765 (w), 740 (m), 720 (w), 700 (w).

$^1$H-NMR(CDCl$_3$, 100 MHz)δ: 1.70 (d, J=7 Hz, 3H), 4.82 (q, J=7 Hz, 1H). 6.8 (br, 1H), 7.00 d, J=7 Hz, 2H), 7.01 (d, J=9 Hz, 1H), 7.09 (d, J=7 Hz, 2H), 8.30 (dd, J=3 & 9 Hz, 1H), 8.82 (d, J=3 Hz, 1H).

FDMS(m/Z): 348(M+).

Elemental analysis: ($C_{15}H_{12}N_2O_8$): 348.262; Calcd.: C: 51.73, H: 3.47, H: 8.04, O: 36.75; Found: C: 52.27, H: 3.38, N: 8.07, O: 36.28.

Example 5

To a stirred solution of known tert-butyl L-(+)-lactate (0.88 g), 4-(2',4'-dichlorophenoxy)phenol (1.54 g) and triphenylphosphine (1.58 g) in dry tetrahydrofuran (58 ml) on an ice bath, diethylazodicarboxylate (0.95 ml) was added dropwise. After the addition, the ice bath was removed and the mixture was further stirred at room temperature for 25 hours. The reaction mixture was evaporated with a rotary evaporator. The residue thus obtained was purified by silica gel chromatography [silica gel 399 g, eluant:ethyl acetate-hexane (1:30)] to give tert-butyl (2R)-(+)-2-[4'-(2",4"-dichlorophenoxy)-phenoxy]propionate as a colorless oily substance (0.98 g). This was left to stand at room temperature under high vacuum (0.25 Torr) for 2 hours and under atmosphere for several days to crystallize. A crystalline substance thus formed was washed with a small amount of hexane and filtered to give colorless crystals.

m.p. 57.0°-57.5° C.

$[\alpha]_D^{25}$+48.1° (C 1.0, MeOH)

IR$\nu_{max}^{nujol}$(cm$^{-1}$): 3050 (w), 2960 (m), 2930(m), 1740 (s), 1500 (s), 1470 (s), 1390 (w), 1365 (m), 1290 (w), 1275 (w), 1255 (m), 1225 (s), 1195 (s), 1155 (s), 1130 (s), 1100 (s), 1050 (m), 1005 (w), 945 (w), 880 (w), 862 (w), 840 (sh), 820 (s), 803 (w), 778 (w), 745 (w), 690 (w).

$^1$H-NMR (CDCl$_3$, 100 MHz)δ:1.44 (s, 9H), 1.57 (d, J=7 Hz, 3H), 4.58 (q, J=7 Hz, 1H), 6.79 (d, J=9 Hz, 1H), 6.88 (s, 4H), 7.13 (dd, J=2 & 9 Hz, 1H), 7.43(d, J=2 Hz, 1H).

FDMS(m/Z): 382, 384, 386 (M+, Peak intensity 9:6:1).

Elemental analysis: ($C_{19}H_{20}Cl_2O_4$): no satisfactory elemental analysis value could be obtained.

To a stirred solution of tert-butyl (2R)-(+)-2-[4'(2",4"-dichloro-phenoxy)phenoxy]propionate thus obtained (0.68 g) in the methylene chloride (9 ml) on an ice bath, trifluoroacetic acid (1.44 ml) was added. After 30 minutes, the ice bath was removed and the mixture was stirred at room temperature for additional 5 hours. The reaction mixture was evaporated under reduced pressure. The residue (0.61 g) was purified by silica gel chromatography [silica gel 24 g, eluant:methanol-chloroform (1:10)] to give a viscous colorless oily substance of (2R)-(+)-2-[4'-(2",4"-dichlorophenoxy)-phenoxy]propionic acid (0.53 g). When placed at −45° C. overnight, the product crystallized but no crystals could be obtained due to their low melting point. After this product was placed at room temperature under high vacuum (0.25 Torr) for 2 hours, its physical data were measured.

$[\alpha]_D^{28} + 30.2°$ (C 1.0, MeOH).

IR$\nu_{max}^{film}$ (cm$^{-1}$): 3600–2200 (br., s), 1715 (s), 1590 (m), 1580 (m), 1465 (s), 1420 (sh), 1375 (m), 1220 (br, s), 1190 (s), 1130 (s), 1095 (s), 1050 (s), 1005 (w), 935 (m), 865 (m), 820 (s), 775 (m), 745 (w), 690 (w).

$^1$H-NMR (CDCl$_3$, 100 MHz)δ-1.66 (d, J=7 Hz, 3 H), 4.74 (q, J=7 Hz, 1H), 6.82 (d, J=9 Hz, 1H), 6.90 (s, 4H), 7.15 (dd, J=2 & 9 Hz, 1H), 7.44 (d, J=2Hz, 1H).

FDMS(m/Z): 326, 328, 330 (M+, Peak intensity 9:6:1).

Elemental analysis (C$_{15}$H$_{12}$Cl$_2$O$_4$): no satisfactory elemental analysis value could be obtained.

What is claimed is:

1. A process for producing an optically active 2-phenoxypropionic acid, which comprises allowing an optically active lactic ester represented by the following formula (I) to react with a phenol represented by the following formula (II) in the co-presence of a reagent A and a reagent B defined below to form an optically active 2-phenoxypropionic ester represented by the following formula (III), and liberating an optically active 2-phenoxypropionic acid represented by the following formula (IV) from the optically active 2-phenoxypropionic ester:

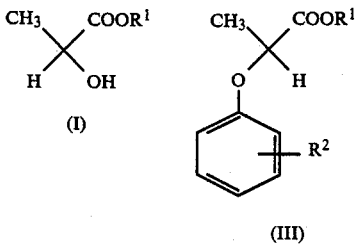

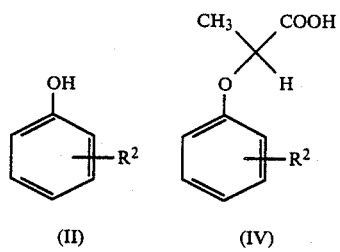

wherein R$^1$ represents a group to form a monovalent ester, which can be eliminated from the compound (III) under weakly basic to acidic conditions and R$^2$ represents a hydrogen atom or 1 to 5 substituents which do not interfere in the reaction between the compounds (I) and (II);

a reagent A being at least one compound selected from the group consisting of trialkylphosphine, trialkylphosphite, triarylphosphine and triarylphosphite; and a reagent B being at least one compound selected from the group consisting of dialkylazodicarboxylate and diarylazodicarboxylate.

2. A process according to claim 1, wherein the reagent A is at least one compound selected from the group consisting of tributylphosphine, trioctylphosphine, triphenylphosphine, triethylphosphite, trimethylphosphite and triphenylphosphite.

3. A process according to claim 1, wherein the reagent B is at least one compound selected from the group consisting of diethylazodicarboxylate, dimethylazodicarboxylate and diphenylazodicarboxylate.

4. A process according to claim 1, wherein the reaction between the optically active lactic ester and the phenol is carried out in an inert solvent selected from the group consisting of tetrahydrofuran, diethyl ether, methylene chloride and benzene.

5. A process according to claim 1, wherein the reaction between the optically active lactic ester and the phenol is commenced with the concentration of the optically active lactic ester being 0.1 to 2 moles and the amounts of the phenol and the reagents A and B each being 1 to 5 moles based on 1 mole of the optically active lactic ester.

6. A process according to claim 1, wherein the liberation of the optically active 2-phenoxypropionic acid is carried out by means of hydrolysis, reductive ester cleavage or hydrogenolysis.

* * * * *